(12) United States Patent
Samkov et al.

(10) Patent No.: US 10,722,361 B2
(45) Date of Patent: Jul. 28, 2020

(54) HEART VALVE PROSTHESIS

(71) Applicants: Alexander V. Samkov, Moscow (RU);
Dmitry V. Cherkesov, Moscow (RU);
Anton D. Solodukhi, Moscow (RU)

(72) Inventors: Alexander V. Samkov, Moscow (RU);
Dmitry V. Cherkesov, Moscow (RU);
Anton D. Solodukhi, Moscow (RU)

(73) Assignee: Alexander V. Samkov, Moscow (RU)

( * ) Notice: Subject to any disclaimer, the term of this patent is extended or adjusted under 35 U.S.C. 154(b) by 84 days.

(21) Appl. No.: 16/037,166

(22) Filed: Jul. 17, 2018

(65) Prior Publication Data
US 2019/0328524 A1 Oct. 31, 2019

(30) Foreign Application Priority Data
Apr. 28, 2018 (RU) ................. 2018116190

(51) Int. Cl.
*A61F 2/24* (2006.01)
*A61B 5/00* (2006.01)
*A61B 5/02* (2006.01)
*A61B 5/021* (2006.01)

(52) U.S. Cl.
CPC ............ *A61F 2/2442* (2013.01); *A61B 5/686* (2013.01); *A61F 2/2472* (2013.01); *A61B 5/021* (2013.01); *A61B 5/02028* (2013.01); *A61B 2562/0204* (2013.01); *A61B 2562/028* (2013.01); *A61B 2562/0223* (2013.01); *A61B 2562/0271* (2013.01); *A61F 2230/0006* (2013.01); *A61F 2250/0092* (2013.01); *A61F 2250/0096* (2013.01)

(58) Field of Classification Search
CPC .................. A61F 2/2442; A61F 2/2472; A61F 2230/0006; A61F 2250/0092; A61F 2250/0096; A61B 5/021; A61B 5/686; A61B 5/02028; A61B 2562/0204; A61B 2562/0223; A61B 2562/0271; A61B 2562/028
See application file for complete search history.

(56) References Cited

U.S. PATENT DOCUMENTS

2008/0033527 A1* 2/2008 Nunez ................ A61B 5/0215
623/1.13
2017/0027689 A1* 2/2017 Marcelli ............. A61B 5/6869

* cited by examiner

*Primary Examiner* — Christopher D. Prone
*Assistant Examiner* — Tiffany P Shipmon
(74) *Attorney, Agent, or Firm* — Aleksandr Smushkovich

(57) ABSTRACT

A heart valve prosthesis is proposed, including a housing, at least one leaflet installed within the housing, at least one sensor and/or valve performance monitoring device. The sensor and/or monitoring device is built into the housing and/or leaflet. In an embodiment, the housing and/or leaflet has an oscillating circuit including an inductor coil connected to the sensor and/or monitoring device. One such coil can be built into the housing, and another coil can be built into the leaflet. In another embodiment, one coil can be built into a first leaflet, and another coil can be built into a second leaflet, wherein the sensor and/or monitoring device determines a degree of opening/closing the leaflets by measuring inductive interconnection between the coils, and operation timing characteristics of the valve. In an embodiment, the valve may include an emission sensor disposed within the leaflet and/or housing capable of detecting the valve's open/closed positions.

14 Claims, 7 Drawing Sheets

HEART VALVE PROSTHESIS

CROSS-REFERENCES TO RELATED APPLICATIONS

This application claims priority under 35 U.S.C. 119 (a) through (d), under the Paris Convention, from a Russian Federation patent application RU2018116190 filed 28 Apr. 2018 hereby entirely incorporated by reference.

FIELD OF THE INVENTION

The claimed invention relates to medical technologies/techniques and can be employed in manufacturing of heart valve prostheses and in monitoring the performance of these prostheses after implantation.

BACKGROUND OF THE INVENTION

Known in the art is a sensor for heart valve prostheses (WO 2016/028583, Feb. 25, 2016). The disclosed sensor is a separate implantable in the heart device being a frame body with sensing elements coupled to it.

Known in the art also a device for monitoring the heart valve performance, the device being an elongate tube connected to the left ventricle of the heart. A blood pressure sensor is attached to the tube (WO 2017/136733, Aug. 10, 2017). The disclosed sensor is a separate implantable device/unit.

Known in the art a device for monitoring physiological parameters of the human body implanted in vivo with various sensors (US 2017086683, Mar. 30, 2017).

In all of the above mentioned devices, their sensors are separate implantable articles, which do not substitute any native body organs and do not fulfill functions of any organs. The shortcoming/imperfection of such devices is that during the entire period of operation their sensor is washed by blood flow, which imposes special requirements on choosing the proper materials for sensor manufacturing and demands additional research assessment of compatibility of these materials with blood and human body tissues. Besides, there are appearing problems of blood clots agglomeration along the parts/components of the implanted devices, which may result in thrombosis, blood vessels occlusion and a patient's death.

The term "sensor" used in the present application may include, without limitation, electrical, temperature, mechanical, acoustical, magnetic, optical sensors and combinations thereof. An example of a combined sensor is the ultrasonic piezo transducer/emitter (electromechanical sensor or electroacoustic sensor depending on the usage variant).

Functionally, the implanted devices may have mechanisms of wireless power supply and wireless communication with the external devices including necessary antenna devices.

SUMMARY OF THE INVENTION

The disclosed invention allows solving the above mentioned problems. The proposed heart valve prosthesis (herein also further called 'valve') comprises: a housing and a number of leaflets, a heart performance monitoring device with sensors integrated into the leaflet or into the housing, at the manufacturing stage. The heart performance monitoring device and the sensors do not contact directly with blood flow or other human body media during operation of the valve. Its proper operation is ensured by methods/devices of wireless electrical power supply and wireless data transmission with their own antennas.

Thus, the present invention allows avoiding any separate additional devices implanted in the body, e.g. diagnostic testers (apart from the valve); the valve's materials have already passed all necessary certification and approbation procedures on compatibility, which minimizes in general the impact of operation of the valve's systems, the monitoring devices and sensors upon functioning of the human organism.

Specifically, the proposed valve is equipped with a number of performance monitoring devices (preferably of a microelectronic/MEMS type, herein further called 'monitoring devices') and/or with sensors, whose functions may include determination of blood temperature, a degree of the leaflets' opening and closing, timing parameters of the leaflets' opening and closing (estimated by measuring of time periods between the leaflets' opening and closing), monitoring the blood pressure, viscosity and monitoring of cleaning the valve's parts by removing blood clots.

The inventive valve comprises a housing (preferably of an annular shape), at least one leaflet installed within the housing, and a number of valve performance monitoring devices (preferably of a microelectronic/MEMS type) and/or sensors, equipped with wireless electrical power supply and wireless data transmission devices furnished with antennas; wherein the monitoring devices and/or sensors, at the manufacturing stage, are integrated (built) into the body of the housing, and/or into the body of the leaflet, and/or into any other part of the valve, and thus do not contact directly with the blood flow and other human body media in the operation mode.

In some preferred embodiments, the housing and/or each leaflet has an oscillating circuit with an inductor coil and a capacitor connected to the performance monitoring device. An emission sensor, for example, an ultrasonic one based on piezo elements, may be disposed (built) in the body of the leaflet and/or in the body of the housing.

The sensors and other devices fulfil the functions of monitoring the blood pressure, temperature, viscosity, operation/performance of the leaflets, and monitoring of cleaning the valve's parts by removing blood clots.

BRIEF DESCRIPTION OF THE DRAWINGS

In the accompanying figures identical elements/parts are identified/designated by identical reference numerals, characters or symbols throughout the drawings.

FIG. 1a-2 is a perspective view of placement of an antenna as a single closed-loop wiring turn in a part/sector of the housing along one side of the monitoring device and/or the sensor.

FIG. 1a-3 is a perspective view of placement of an antenna as a single closed-loop wiring turn in a part/sector of the housing around the monitoring device and/or the sensor.

FIG. 3a-1 is a top plan view of an example of placement of an emission sensor in the leaflet.

FIG. 3a-2 is a side view; wherein the leaflet is in a closed position, the emission sensor in the leaflet is emitting aside from the housing.

FIG. 3a-3 is a side view; wherein the leaflet is in an open position, the emission sensor in the leaflet is emitting towards the housing.

DETAILED DESCRIPTION OF THE INVENTION

Figures 1, 1A:
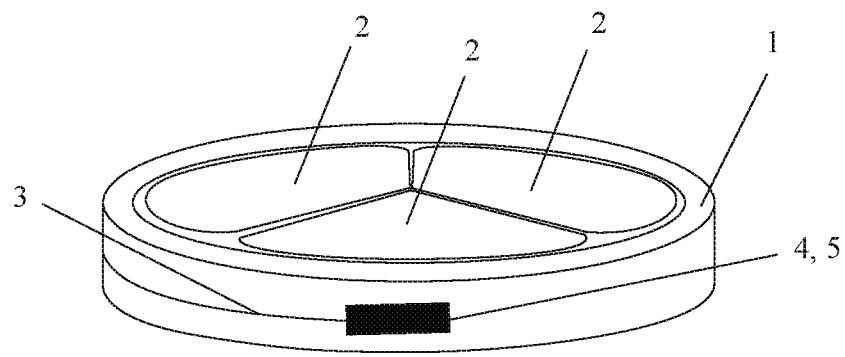
FIG. 1a-1 is a perspective view of placement of an antenna as a single open circuit wiring turn in a part/sector of a housing of the inventive heart valve, along one side of a monitoring device and/or a sensor.

While the invention may be susceptible to embodiment in different forms, there are described in detail herein below, specific embodiments of the present invention, with the understanding that the instant disclosure is to be considered an exemplification of the principles of the invention, and is not intended to limit the invention to that as described herein.

According to preferred embodiments of the disclosed invention, the prosthetic heart valve comprises a housing 1, at least one leaflet 2 installed within the housing and a number of valve performance monitoring devices (monitoring devices 5) with a number of additional active or passive sensors 4 equipped with wireless electrical power supply and wireless data transmission devices (with their own antennas 3—common or separate/independent); all the devices are integrated (built-in) into the housing' s body, and/or into the leaflet's body, and/or other parts of the valve. The housing's and its leaflets' volumetric dimensions allow deploying therein a certain number of diagnostic testers, while their linear dimensions allow deploying therein various types of antennas both for a remote power supply and for an informational exchange with an external device.

The substance of the invention is explained by the drawings related to the tri-leaflet prosthetic heart valve (further named 'valve'). The sensors 4 and the monitoring devices 5 may be built into the housing 1 (preferably of an annular shape) or in the leaflet 2 depicted in FIGS. 1a-1, 1a-2, 1a-3, 1b, 1c, 1d and FIGS. 3a-1, 3a-2, 3a-3, 3b, 3c, 3d. The sensors 4 and/or the monitoring devices 5 are equipped with the antennas 3.

Figures 1, 1A, 2:
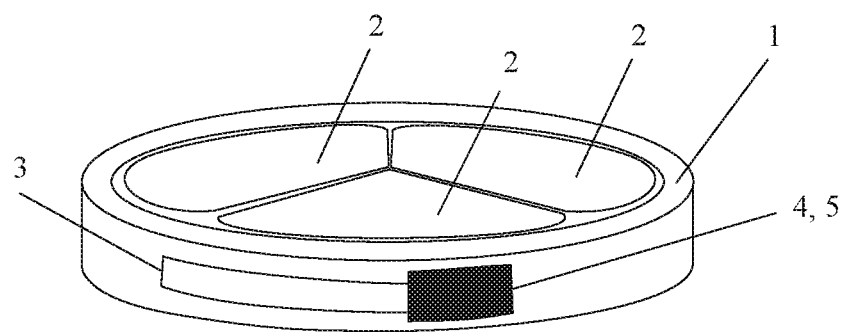
Figures 1, 1A, 2, 3:
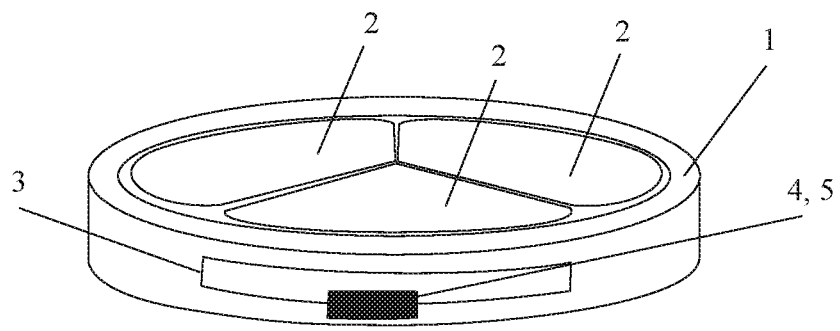
Figure 1B:
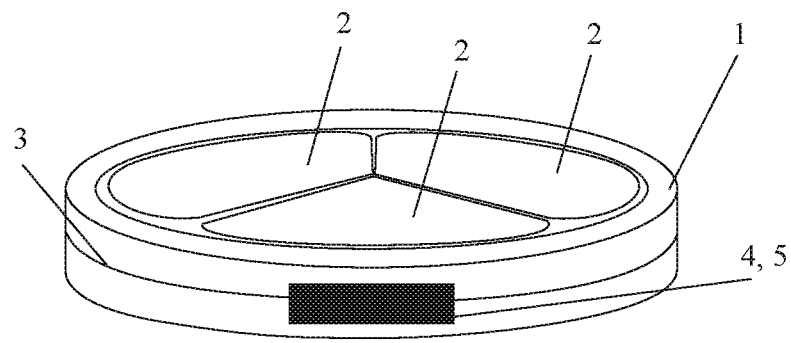
FIG. 1b is a perspective view of placement of an antenna as a single closed-loop wiring turn around the entire housing.
Figure 1C:
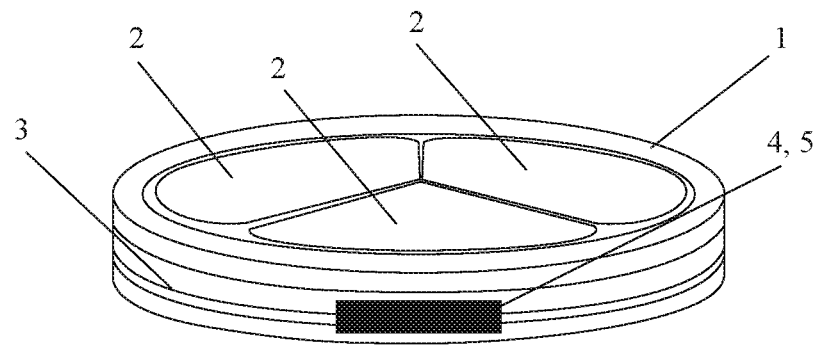
FIG. 1c is a perspective view of placement of an antenna as a closed-loop multi-turn wiring around the entire housing.
Figure 1D:
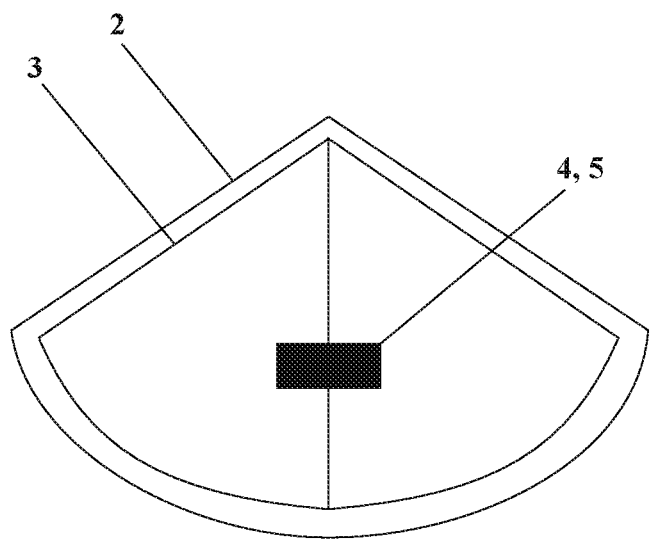
FIG. 1d is a perspective view of placement of an antenna as a closed-loop multi-turn wiring in a leaflet of the heart valve.
Figure 2A:
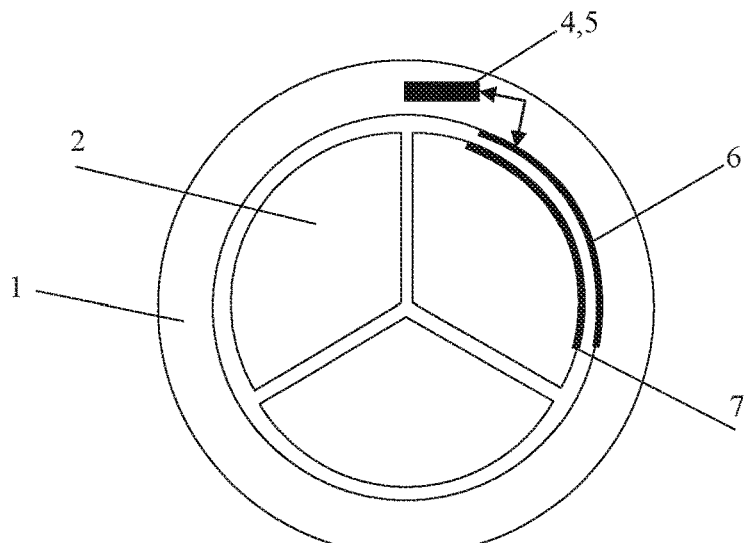
FIG. 2a is a top plan view of placement of inductor coils in the housing and in the oppositely situated leaflet.
Figure 2B:
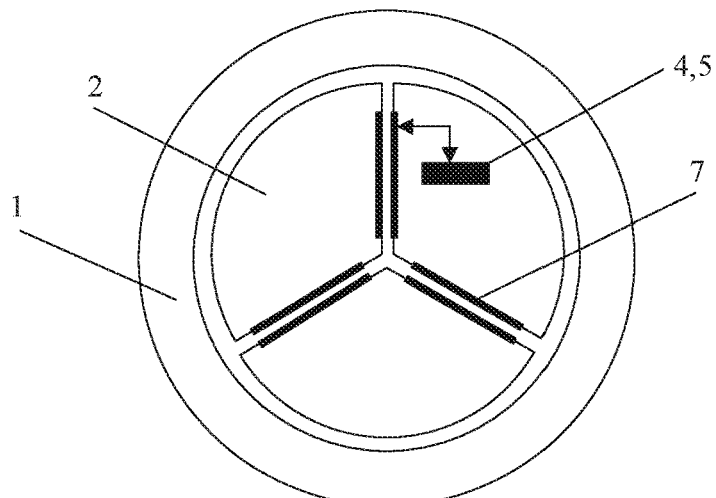
FIG. 2b is a top plan view of placement of inductor coils along the opposite edges in the leaflets.
Figure 2C:
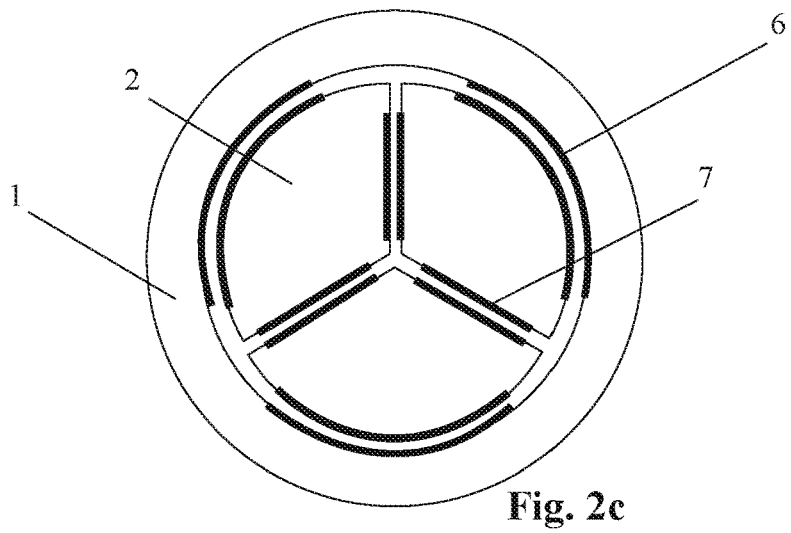
FIG. 2c is a top plan view of placement of inductor coils in the housing along all the edges in the leaflets.

Examples of placement of the antennas 3 of the sensors 4 and the monitoring devices 5 in the housing 1 and the leaflets 2 are shown in FIGS. 1a-1, 1a-2, 1a-3, 1b, 1c (for the housing 1) and in FIG. 1d (for the leaflet 2). FIGS. 1a-1, 1a-2, 1a-3 demonstrate the placement of various types of the antenna 3 in one of the housing's sectors.

To enhance efficacy of the antenna 3 by enlarging/expanding its dimensions, the antenna 3 may be deployed along the full circumference of the housing 1 (shown in FIG. 1b) as a single closed-loop or open circuit wiring turn. To further enhance the antenna's capability, it may be configured as a multi-turn loop (FIG. 1c). A rather large area of the surface of the leaflets 2 and a long perimeter of each leaflet 2 allow for placement of the antenna 3 directly in the leaflet 2. One of the possible variants is shown in FIG. 1d.

The housing 1 and/or each leaflet 2 may be equipped with an oscillating circuit including an inductor coil 6 or 7 and a capacitor (not shown) connected to the monitoring device 5 and/or the sensor 4. By assessing inductive interconnection between the inductor coils 6 or 7 at the moment of opening/closing the leaflets 2, it is possible to determine a degree of opening and closing of the leaflets 2 and timing characteristics of operation of the valve.

FIGS. 2 (2a, 2b, 2c) show possible options of placement of the inductor coils 6 and 7 to determine the degree of opening/closing the leaflets 2 (2a—placement of the inductor coils 6 in the housing 1 and opposite to the inductor coils 7 disposed in the opposite situated leaflet 2; 2b—placement of the inductor coils 7 along the opposite edges in the leaflets 2; 2c—placement of the inductor coils 6 and 7 in the housing 1, in the opposite situated leaflet 2 and along the opposite edges in the leaflets 2).

During the opening of the leaflets, the distances between the inductor coils 6 and 7 both in the leaflets 2, and between the leaflets 2 and the housing 1, are growing, thereby minimizing inductive interconnection between the circuits; while when the leaflets 2 are completely closed the interconnection between the circuits is maximal. Accordingly, the monitoring device 5 assesses the circuits' interconnection and provides for determination of a degree of opening and closing the leaflet.

Calibration of measurements may be effected prior to implantation of the valve, if necessary. The calibration may also be effected immediately after the implantation, to evaluate corrections related to nonzero physical parameters of body/blood and their influence on the interconnection between the circuits.

In another preferred embodiment, additional sensors 4 may be integrated into the housing 1 or into the leaflet 2, which may be both self-sufficient and may work independently from the monitoring device 5 (all necessary electronic circuits/components can be arranged inside the body of the sensor 4); or, optionally, the additional sensors 4 may be connected with the monitoring device 5, which allows determining not only a degree of opening of the leaflets 2 and timing characteristics of performance of the valve, but also a number of additional parameters, e.g. blood temperature and viscosity, mechanical and physical parameters of the valve's housing and leaflets, etc.

FIGS. 3a-1, 3a-2, 3a-3, 3b, 3c, 3d show possible locations of emission sensors 8 (in the leaflet, in an emission/transmission mode), emission sensors 10 (in the housing 1) and emission sensors 11 (receivers, transmitters or transceivers) for determination of a degree of opening the leaflets and for determination of physical/chemical characteristics of the blood circulatory system.

The emission sensors 8, 10 and 11 may be both electro-mechanical e.g. based on piezo electrical elements as well as electrical e.g. based on light emitting diodes (LEDs)/receiving photodiodes of various wave length ranges including monochrome emitters (lasers) and others.

Examples of placement of the emission sensor 8 in the leaflet 2 and their operation modes are shown in FIGS. 3*a*-1, 3*a*-2, 3*a*-3. When the leaflet 2 is in a closed position, the sensor 8 (its transmitting part), disposed in the leaflet 2, emits into a patient's body aside from the valve housing 1, a reflected beam is absent.

When the leaflet 2 is fully open, an emitted beam 9 reaches the housing 1, and then is either reflected from the housing 1 and can be detected by a receiving part of the sensor 8 in the leaflet 2, or is detected by a separate receiver in the housing 1.

Figures 1, 3A:
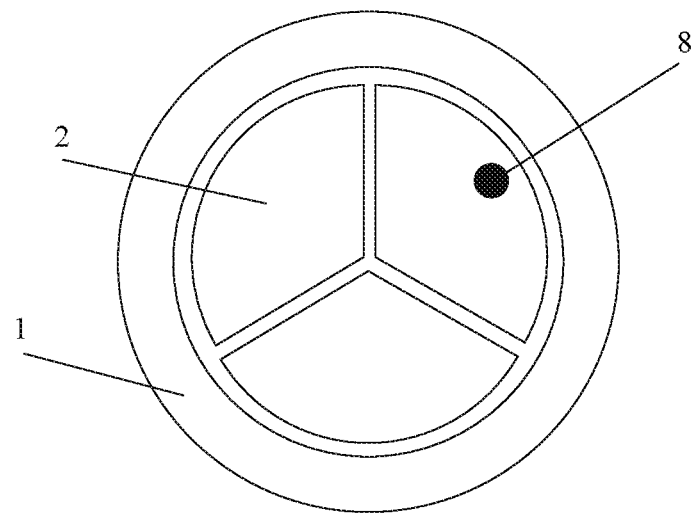
Figures 2, 3A:
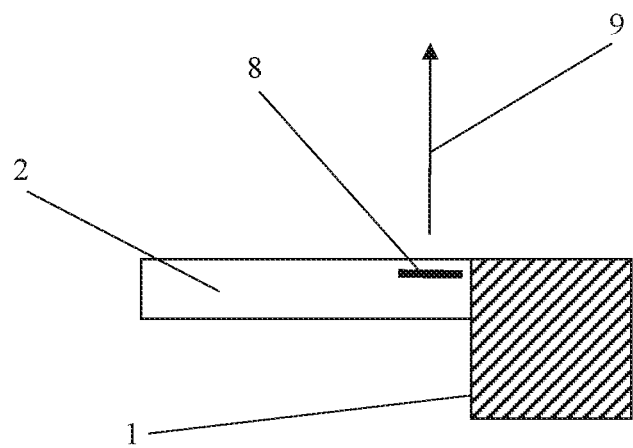
Figures 3, 3A:
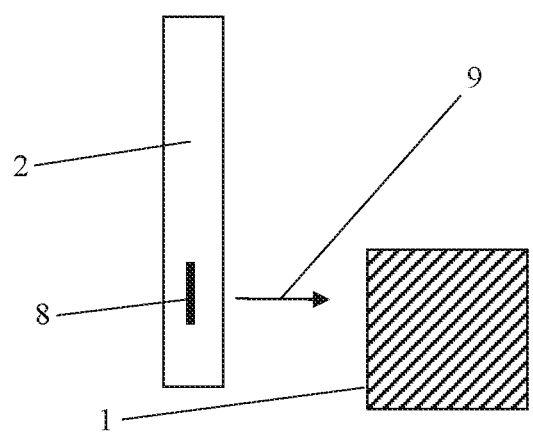
Figure 3B:
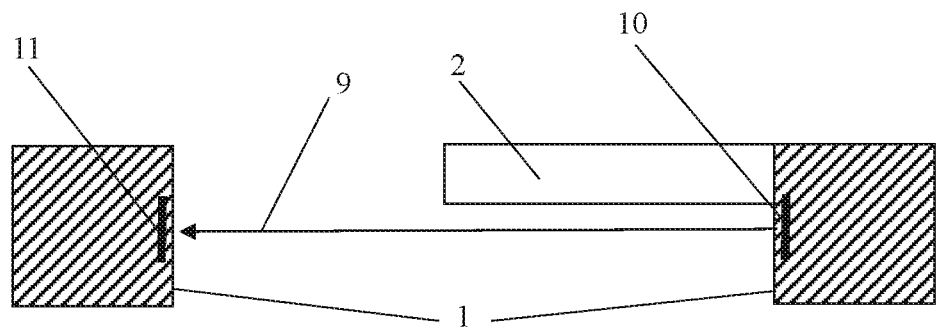
FIG. 3b is a side view; the leaflet is in a closed position, wherein the emission sensor in the right side of the housing (transmitter) is emitting towards the sensor (receiver) in the left part of the housing without interference.
Figure 3C:
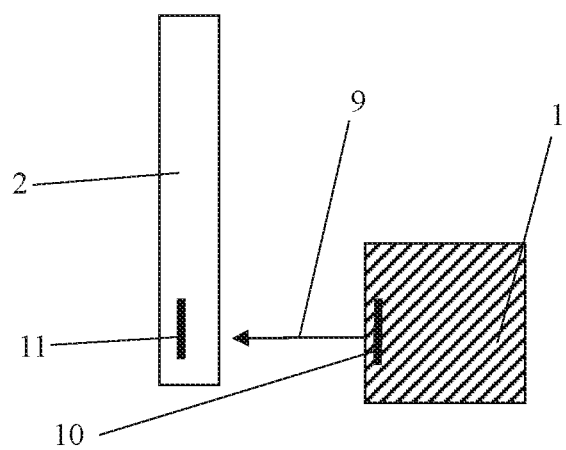
FIG. 3c is a side view; wherein the leaflet is in an open position, the emission of the sensor in the right side of the housing (transmitter) reaches the sensor (receiver) in the leaflet.
Figure 3D:
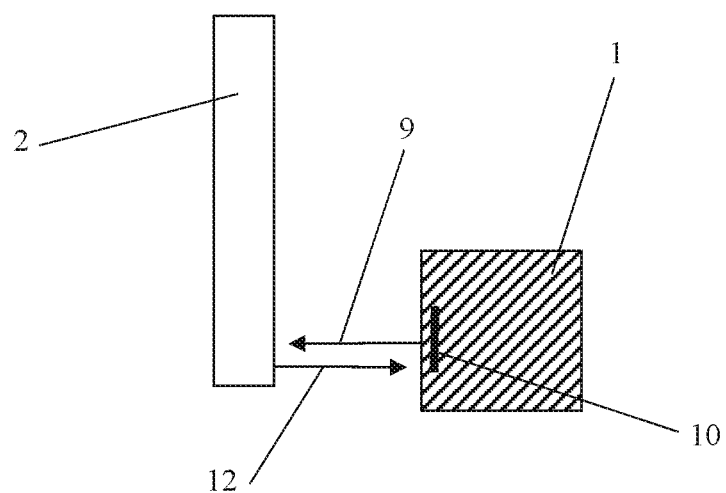
FIG. 3d is a side view; the leaflet is in an open position, wherein the emission of the sensor in the right side of the housing (transmitter) is reflected from the leaflet and returns to the sensor (receiver) in the right side of the housing.

Another example of placement of the emission sensors 10 (transmitting part of the transceiver) and emission sensors 11 (receiving part) in the housing 1 is shown in FIG. 3*b*. The emission sensor (transmitting part of the transceiver) 10 is disposed in one side of the housing 1; when the leaflet 2 is in a closed position, the emitted beam 9 can be detected on the opposite side of the housing 1 by the emission sensor (receiver) 11; when the leaflet 2 is fully open, the emitted beam 9 can be detected by the emission sensors 11 (receiving part) in the leaflet 2 (FIG. 3*c*), or a reflected beam 12 can be detected by the receiving part of the emission sensor (transceiver) 10 contained in the housing 1 (FIG. 3*d*).

An ultrasonic electromechanical emitter, disposed within the valve, may also carry out the function of valve cleaning from blood clots or preventing such clots formation. The ultrasonic emitter can be deployed inside all parts of the valve: in the housing 1 and/or in each leaflet 2. The regular use of the emitter will prevent the blood clots agglomeration along the valve's elements, a probable thrombosis or a deviation of the valve operation from the normal mode in the future.

A temperature sensor will allow monitoring a patient's blood temperature. Placement of such temperature sensors and the ultrasonic cleaning emitter does not require illustration being a designer's choice.

The presented drawings do not illustrate the placement of sensors and emitters within a bi-leaflet valve and a single leaflet valve. Their configuration and functioning will be understood by those skilled in the art from analogy with the above description for the tri-leaflet valve.

We claim:

1. A heart valve prosthesis comprising: a housing defining a clearance therein; at least one leaflet installed within the housing and capable of opening and closing the clearance; at least one sensor A built into the housing, and at least one valve performance monitoring device built into the housing; said housing includes at least one segment; and at least one sensor B built into said at least one leaflet;

wherein:

the at least one sensor A includes a first inductor built into the respective at least one segment;

the at least one sensor B includes a second inductor built into the respective at least one leaflet;

the first inductor is substantially connected to the at least one valve performance monitoring device;

each pair of the first inductor and the second inductor is positioned along opposite edges of the respective at least one segment and the respective at least one leaflet forming inductive interconnection between the first inductor and the second inductor;

and wherein:

the at least one sensor A, and/or the at least one sensor B, and/or the at least one valve performance monitoring device determine a degree of opening and closing of said at least one leaflet and timing characteristics of operation of the heart valve prosthesis by measuring the inductive interconnection for said each pair of the first inductor and the second inductor that indicates a current spatial position of the at least one leaflet.

2. The valve of claim 1 wherein: said at least one valve performance monitoring device is further equipped with at least one antenna arranged according to one of the following configurations:

the at least one antenna is a single open or a single closed circuit wiring turn placed in a segment of said housing, along one side of said at least one sensor and/or said at least one valve performance monitoring device; the at least one antenna is a single open or a single closed circuit wiring turn placed in a segment of said housing, around one side of said at least one sensor and/or said at least one valve performance monitoring device; the at least one antenna is a closed-loop multi-turn wiring around the housing; and the at least one antenna is a closed-loop multi-turn wiring placed in the at least one leaflet.

3. The valve of claim 1 wherein: said at least one sensor additionally includes a temperature sensor.

4. The valve of claim 1 wherein: said at least one sensor and/or said at least one valve performance monitoring device is equipped with a number of wireless data transmission devices.

5. The valve of claim 1, wherein said at least one leaflet includes at least a leaflet CL and a leaflet DL being adjacent to the leaflet CL; said valve further comprising at least one additional sensor C built into the leaflet CL and at least one additional sensor D built into the leaflet DL, and at least one additional valve performance monitoring device built into the leaflet CL and/or into the leaflet DL;

wherein: the leaflet CL defines a third edge, and the leaflet DL defines a fourth edge adjacent to the third edge;

the additional sensor C further includes a third inductor positioned along the third edge and the additional sensor D further includes a fourth inductor positioned along the fourth edge; the third inductor and the fourth inductor form a pair of inductive interconnection therebetween; the at least one additional valve performance monitoring device is connected to the third inductor and/or to the fourth inductor;

and wherein:

at least one sensor of the sensors A and B, and/or at least one sensor of the additional sensors C and D, and/or the at least one valve performance monitoring device and/or the at least one additional valve performance monitoring device determine a degree of opening and closing of said at least one leaflet and timing characteristics of operation of the heart valve prosthesis by measuring the inductive interconnection for said each pair of the first inductor and the second inductor and for said each pair of the third inductor and the fourth inductor.

6. The valve of claim 5 wherein: said at least one sensor A, and/or said at least one sensor B, and/or said at least one additional sensor C, and/or said at least one additional sensor D, and/or said at least one valve performance monitoring device are further equipped with at least one antenna arranged according to one of the following configurations:

the at least one antenna is a single open or a single closed circuit wiring turn placed in the segment of said housing, along one side of the sensor A, and/or the sensor B, and/or the sensor C, and/or the sensor D, and/or said at least one valve performance monitoring device; the at least one antenna is a single open or a single closed circuit wiring turn placed in the segment of said housing, around one side of the sensor A, and/or the sensor B, and/or the sensor C, and/or the sensor D, and/or said at least one valve performance monitoring device; the at least one antenna is a closed-loop multi-turn wiring around the housing; and the at least one antenna is a closed-loop multi-turn wiring placed in the sensor A, and/or the sensor B, and/or the sensor C, and/or the sensor D.

7. A heart valve prosthesis comprising: a housing defining a clearance therein; at least two leaflets installed within the housing and capable of opening and closing the clearance; at least two sensors each built into one leaflet of said at least two leaflets, and at least one valve performance monitoring device built into at least one leaflet of said at least two leaflets;
wherein:
a leaflet AL of said at least two leaflets defines a first edge, and a leaflet BL of said at least two leaflets, being adjacent to the leaflet AL, defines a second edge adjacent to the first edge;
a sensor A of the at least two sensors includes a first inductor built into the leaflet AL, and a sensor B of the at least two sensors includes a second inductor built into the leaflet BL;
the first inductor is positioned along the first edge; the second inductor is positioned along the second edge;
the first inductor and the second inductor form a pair of inductive interconnection therebetween;
the at least one valve performance monitoring device is connected to the first inductor and/or to the second inductor;
and wherein:
the at least two sensors and/or the at least one valve performance monitoring device determine a degree of opening and closing of said at least two leaflets and timing characteristics of operation of the heart valve prosthesis by measuring the inductive interconnection for said each pair of the first inductor and the second inductor that indicates current spatial positions of the at least two leaflets.

8. The valve of claim 7 wherein: one sensor of said at least two sensors and/or said at least one valve performance monitoring device is further equipped with at least one antenna arranged according to one of the following configurations:
the at least one antenna is a single open or a single closed circuit wiring turn placed in the respective leaflet of the at least two leaflets, along one side of said at least one sensor and/or said at least one valve performance monitoring device; the at least one antenna is a single open or a single closed circuit wiring turn placed in the respective leaflet of the at least two leaflets, around one side of one of said at least two sensors and/or said at least one valve performance monitoring device; the at least one antenna is a closed-loop multi-turn wiring around the respective leaflet of the at least two leaflets; and the at least one antenna is a closed-loop multi-turn wiring placed in the respective leaflet of the at least two leaflets.

9. The valve of claim 7 wherein: at least one of said at least two sensors additionally includes a temperature sensor.

10. The valve of claim 7 wherein: said at least two sensors and/or said at least one valve performance monitoring device are further equipped with a number of wireless data transmission devices.

11. A heart valve prosthesis comprising: a housing defining a clearance therein; at least one leaflet installed within the housing and capable of opening and closing the clearance; at least one valve performance monitoring device built into the housing and/or into the at least one leaflet; at least one housing emission sensor built into the housing and at least one leaflet emission sensor built into the at least one leaflet; the housing emission sensor and/or the leaflet emission sensor are connected to said at least one valve performance monitoring device;
wherein:
said at least one housing emission sensor further includes a transmission part capable of transmitting a beam to the at least one leaflet and/or a receiving part capable of receiving a beam from the at least one leaflet emission sensor, and
said at least one leaflet emission sensor further includes a receiving part capable of receiving a beam from the at least one housing emission sensor and/or a transmission part capable of transmitting a beam to the housing;
wherein: either
when said at least one leaflet is in a closed position, the beam is transmitted from said at least one leaflet emission sensor into a patient's body aside from the housing, while when said at least one leaflet is in an open position, the beam is transmitted from said at least one leaflet emission sensor at the housing, detected by the receiving part of said at least one housing emission sensor, and processed by the at least one valve performance monitoring device thereby determining a degree of opening and closing of said at least one leaflet and timing characteristics of operation of the heart valve prosthesis; or
when said at least one leaflet is in a closed position, the beam is transmitted from said at least one housing emission sensor into a patient's body aside from the at least one leaflet, while when said at least one leaflet is in an open position, the beam is transmitted from said at least one housing emission sensor at the at least one leaflet, detected by the receiving part of said at least one leaflet emission sensor, and processed by the at least one valve performance monitoring device thereby determining a degree of opening and closing of said at least one leaflet and timing characteristics of operation of the heart valve prosthesis.

12. The valve of claim 11 wherein: said at least one valve performance monitoring device is further equipped with at least one antenna arranged according to one of the following configurations:
the at least one antenna is a single open or a single closed circuit wiring turn placed in the respective at least one leaflet, along one side of said at least one valve performance monitoring device; the at least one antenna is a single open or a single closed circuit wiring turn placed in the respective at least one leaflet, around one side of said at least one valve performance monitoring device; the at least one antenna is a closed-loop multi-turn wiring around the respective at least one leaflet; and the at least one antenna is a closed-loop multi-turn wiring placed in the respective at least one leaflet.

13. The valve of claim 11 wherein: said at least one valve performance monitoring device is equipped with a number of wireless data transmission devices.

14. The valve of claim 11 wherein: said at least one emission sensor is of an ultrasonic type based on piezo elements or of an optical type.

* * * * *